United States Patent
Zoumas et al.

[11] Patent Number: 5,837,227
[45] Date of Patent: Nov. 17, 1998

[54] USE OF COCOA BUTTER OR PARTIALLY HYDROLYZED COCOA BUTTER FOR THE TREATMENT OF BURNS AND WOUNDS

[75] Inventors: Barry L. Zoumas; Stanley M. Tarka, both of Hershey; J. Michael McKim; Bryan J. Simmons, both of Elizabethtown; James G. Marks, Jr., Hershey; Michael Santanna, Harrisburg, all of Pa.

[73] Assignee: Hershey Foods Corporation, Hershey, Pa.

[21] Appl. No.: 578,456

[22] Filed: Dec. 26, 1995

[51] Int. Cl.$^6$ .................................................. A61K 35/78
[52] U.S. Cl. ..................................... 424/78.06; 424/78.08
[58] Field of Search ..................... 426/33, 45; 424/78.06

[56] References Cited

U.S. PATENT DOCUMENTS

| | | |
|---|---|---|
| 3,609,102 | 9/1971 | Schlossman . |
| 3,654,327 | 4/1972 | Castner . |
| 3,856,936 | 12/1974 | Vick et al. . |
| 3,860,702 | 1/1975 | Buell . |
| 3,862,197 | 1/1975 | Castner . |
| 3,878,297 | 4/1975 | Vick . |
| 4,165,385 | 8/1979 | Lefebvre ................................. 514/783 |
| 4,450,292 | 5/1984 | Christidis et al. . |
| 4,454,118 | 6/1984 | Johnson . |
| 4,454,159 | 6/1984 | Musher ..................................... 514/21 |
| 4,537,776 | 8/1985 | Cooper . |
| 4,707,354 | 11/1987 | Garlen et al. . |
| 4,784,849 | 11/1988 | Tutsky . |
| 4,828,825 | 5/1989 | Weber et al. . |
| 4,999,185 | 3/1991 | Takemori et al. ...................... 426/631 |
| 5,009,969 | 4/1991 | Miller ........................................ 424/59 |
| 5,019,604 | 5/1991 | Lemole .................................. 523/105 |
| 5,039,516 | 8/1991 | Goodman et al. ........................ 424/59 |
| 5,045,308 | 9/1991 | Spiegel et al. ............................ 424/61 |
| 5,057,497 | 10/1991 | Calam et al. . |
| 5,112,613 | 5/1992 | Honda et al. . |
| 5,141,741 | 8/1992 | Ishida et al. . |
| 5,188,831 | 2/1993 | Nicoll et al. ............................ 424/401 |
| 5,208,012 | 5/1993 | Sudo et al. . |
| 5,216,033 | 6/1993 | Pereira et al. ............................ 514/63 |
| 5,219,558 | 6/1993 | Woodin, Jr. et al. ..................... 424/59 |
| 5,223,250 | 6/1993 | Mitchell et al. . |
| 5,229,130 | 7/1993 | Sharma et al. . |
| 5,232,691 | 8/1993 | Lemole . |
| 5,306,486 | 4/1994 | McCook et al. .......................... 424/59 |

FOREIGN PATENT DOCUMENTS

| | | |
|---|---|---|
| 1182463 | 5/1968 | United Kingdom . |
| 9306737 | 4/1993 | WIPO . |

*Primary Examiner*—Peter F. Kulkosky
*Attorney, Agent, or Firm*—Scully, Scott, Murphy & Presser

[57] ABSTRACT

The present invention is directed to a method of treating wounds and burns on the skin of a warm-blooded animal which comprises applying to the area of the skin that is injured a medicament containing cocoa butter or partially hydrolyzed cocoa butter.

26 Claims, 2 Drawing Sheets

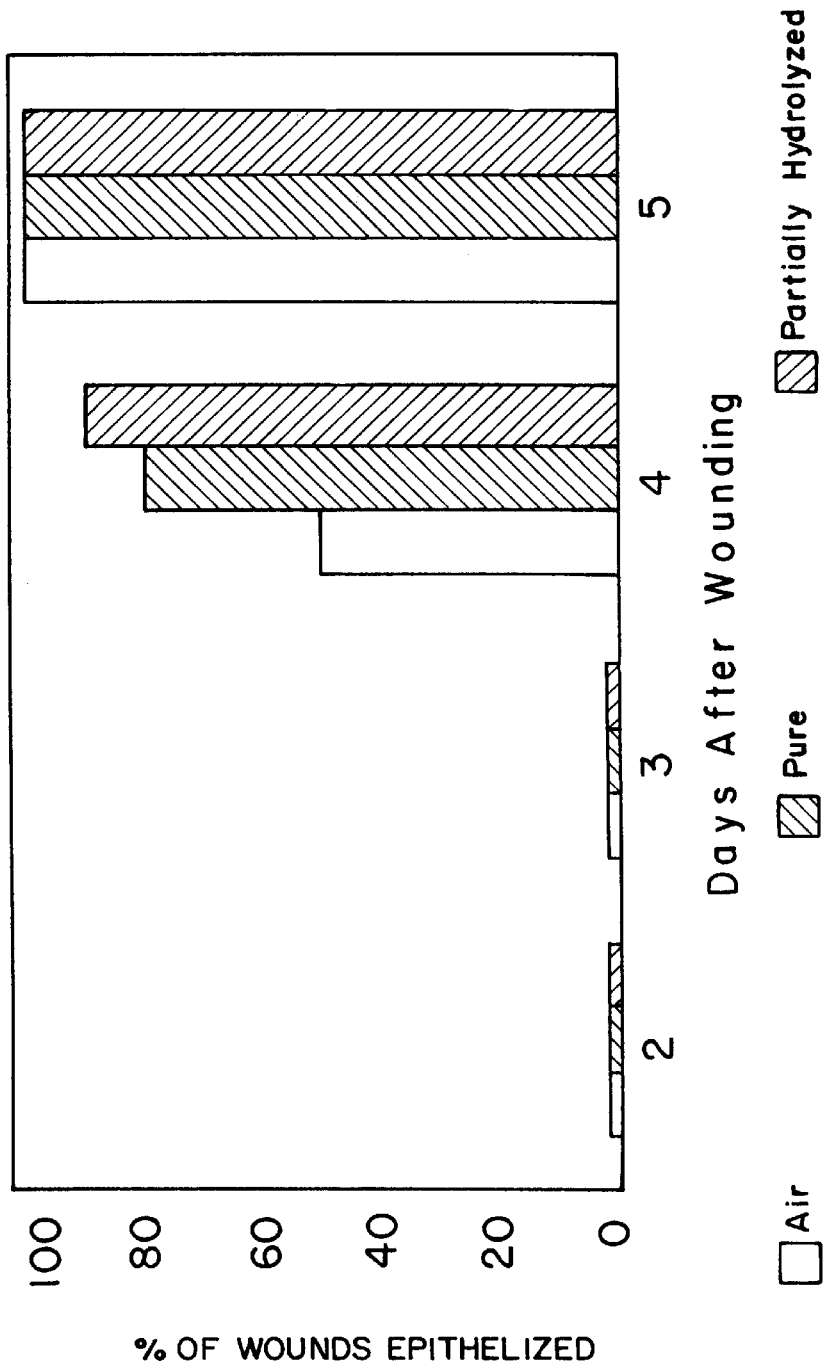

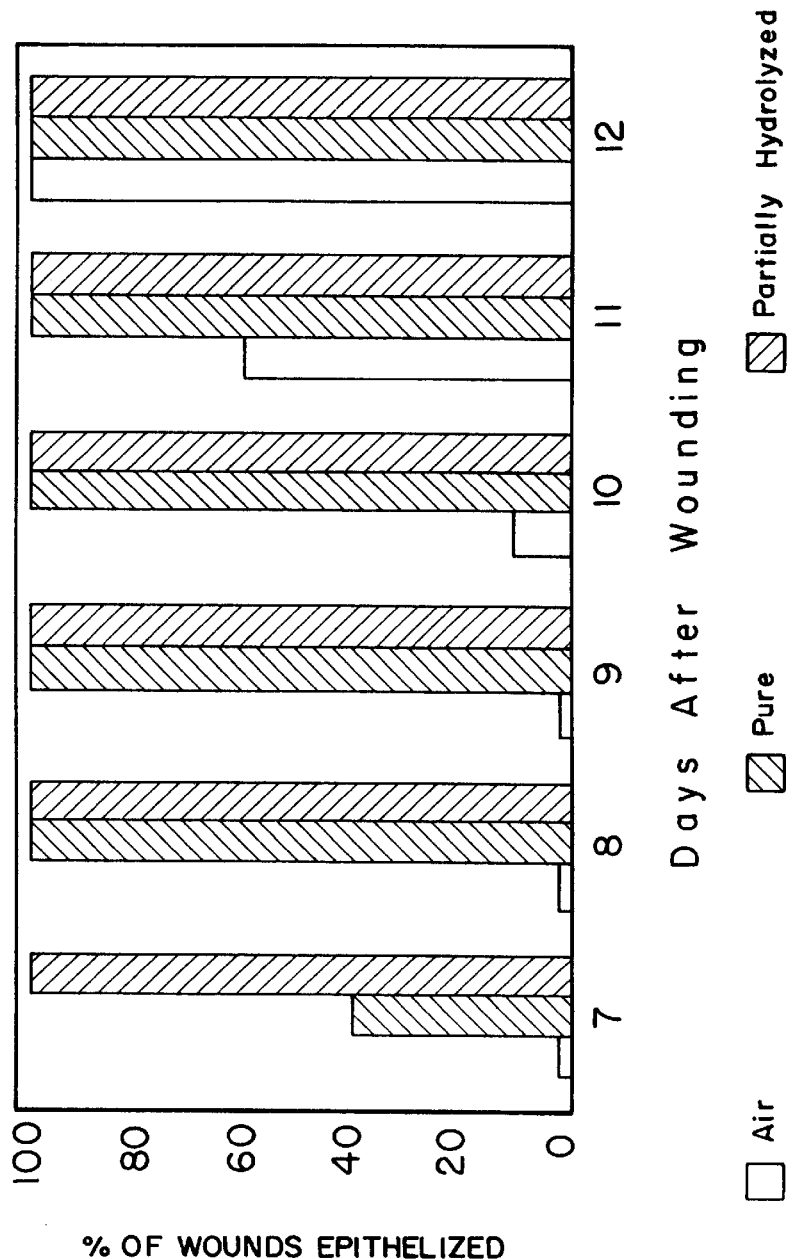
FIG. 2: The Effect of Partially Hydrolyzed Cocoa Butter Emulsion and Pure Cocoa Butter on Burn Wound Healing ＃ USE OF COCOA BUTTER OR PARTIALLY HYDROLYZED COCOA BUTTER FOR THE TREATMENT OF BURNS AND WOUNDS

FIELD OF THE INVENTION

The present invention is directed to the use of cocoa butter or partially hydrolyzed cocoa butter emulsion for the treatment of burns and skin wounds in warm-blooded animals, such as mammals and especially humans.

BACKGROUND OF THE INVENTION

Millions of people in the United States have been afflicted with thermal burns (i.e. burns caused by fire, hot liquid, steam or other hot vapors) or wounds and lacerations caused by cuts or by various utensils or instruments. Even in the most mild cases, people experience some degree of pain. In addition, depending upon the severity and the extent of the wound or burn, there is a wide range of injury that can occur to the skin.

Skin is a structurally complex membrane consisting of several layers, such as *Strateum corneum*, epidermis, epidermis-dermis junction, and the dermis. Thus the wound or burn may damage just the surface of the skin or may extend through the entire thickness of the skin to the subcutaneous tissue. The types of damages occurring from burns or wounds have been classified into various groups. For example, with respect to thermal burns, there is what is medically called "first degree burn" in which the skin is reddened and becomes tender, "second degree burn" in which the skin is blistered and a "third degree burn" where there is extensive tissue damage. Just as with burns, there are also different types of wounds, for example, there is an "incised wound" which is a wound made by a cutting instrument, a "lacerated wound" which is one in which the tissues are torn or mangled by a dull or blunt instrument; an "open wound" in which the wound communicates with the atmosphere by direct exposure; a "penetrating wound" which is caused by sharp, usually slender objects such as a nail or icepick which passes through the skin into the underlying tissues; a "perforating wound" which is a penetrating wound extending into the viscus or bodily cavity; a "puncture wound" which is a type of penetrating wound made by a pointed instrument or a "subcutaneous wound" in which involves damage to only the skin and subcutaneous tissues.

Obviously, the amount and extent of injury to the skin will affect the length of time it take to heal and the pain and distress felt by the victim. The amount of injury to the skin is determined by various factors. These factors include, inter alia, the type of injury, the depth of injury and the extent of the area of the skin that is injured. For example, if the injury is just to the skin, then less treatment would be required than if the injury is to the entire thickness of the skin or if the injury penetrates deeper and involves other tissues, including nerves, bones and blood vessels, or even underlying tissue.

In any one of these cases, the victim wishes to have a medicament that would heal the wound or burn to the skin as quickly as possible, minimize the discomfort level and minimize the risk of infection by bacteria, fungus or other microorganisms.

The present application is directed to medicaments that would satisfy these objectives and therefore be useful for treating thermal burns and cuts and wounds of the kinds described hereinabove.

SUMMARY OF THE INVENTION

The present invention is directed to the use of medicaments containing cocoa butter or partially hydrolyzed cocoa butter for the treatment of skin wounds and burns in warm blooded animals.

BRIEF DESCRIPTION OF THE DRAWINGS

FIG. 1 is a graphical representation of the effect of cocoa butter and partially hydrolyzed cocoa butter emulsion on partial thickness wound healing.

FIG. 2 is a graphical depiction of the effect of cocoa butter and partially hydrolyzed cocoa butter emulsion on burn wound healing.

DETAILED DESCRIPTION OF THE INVENTION

The present inventors have surprisingly found that the use of cocoa butter or partially hydrolyzed cocoa butter emulsion is useful for treating and healing burns and wounds in which there is damage to the skin. As defined herein, the skin includes the various layers described hereinabove. Thus, the present invention is used to treat injury that is on the surface of the skin or injury that penetrates the layers of the skin, i.e., the epidermis and dermis up to but not including the subcutaneous tissue or the fat surrounding the tissue. If the wound or burn does not extend to the subcutaneous layer or fat, it is considered, for purposes of discussion, a "partial thickness" wound or burn. The present invention therefore is useful in treating partial thickness wounds or burns.

As used herein, the term "burns" refers to the burns associated with thermal burns and solar burns. Especially with respect to thermal burns, it consists of the first degree and second degree, and full thickness burns that were discussed hereinabove.

The term "wound" refers to a bodily injury caused by cuts or incisions, or sores, scratches, and the like in which there is an opening or puncture of the skin, i.e., the skin is broken. It also includes bedsores that develop in patients who have been bedridden for a long period of time. The term also encompasses scratches caused by flowers with sharp needles or thorns, e.g. roses, or inflicted by animals including humans, as well as bites from animals or humans in which the skin is broken. The term also includes, but is not limited to, the incised wound, the lacerated wound, the penetrating wound, the open wound, the perforated wound, the puncture wound, the subcutaneous wound and the like.

Cocoa butter, as used herein, is the fat obtained by subjecting chocolate liquor to hydraulic pressure. It has been given various definitions by different companies or agencies. As defined by the FDA, it is the edible fat obtained from cocoa beans either before or after roasting. U.S. Pharmacopeia defines cocoa butter as the fat obtained from the roasted seed of *Theobroma cacao Linne*. The Codex Committee on Cocoa and Chocolate products defines cocoa butter as the fat produced from one or more of the following: cocoa beans, cocoa nibs, cocoa mass (chocolate liquor), cocoa cake, expeller cake or cocoa dust (fine) by a mechanical process and/or with the aid of permissible solvents. As used herein, the term "cocoa butter" incorporates all of these definitions.

Cocoa butter is composed mainly of glycerides of stearic, palmitic and oleic fatty acids. The triglyceride structure of cocoa butter is, by weight, about 3% trisaturated; 22% monounsaturated-oleodistearin; 57% oleopalmitostearin; 4% oleodipalmitin; 6% diunsaturated stearodiolefin, 7% palmitodiolefin and 1% triunsaturated, triolein. There are six crystalline types of cocoa butter, but the four basic forms are gamma, alpha, beta and beta prime. All these forms of cocoa butter can be used in the present invention or can be used to make the partially hydrolyzed cocoa butter emulsion described hereinbelow.

Cocoa butter is prepared by conventional means known to one skilled in the art, especially the chocolate art. A method for its preparation is by subjecting chocolate liquor to hydraulic pressure. Chocolate liquor, in turn, is prepared by conventional means, by the steps of cleaning the cocoa bean, roasting the bean, winnowing and grinding. More specifically, the first step in the process of making chocolate liquor is cleaning the cocoa beans and removing foreign objects therefrom.

The cocoa beans next undergo a roasting step. This is the step where chocolate flavor is normally developed. It is essentially a cooking step which promotes reactions of the latent flavor precursors such as the proteins, amino acids and reducing sugars, organic acids and other unidentified compounds in the cocoa bean to form products which are highly flavored. The roasting conditions are adjusted to produce different types of flavor. For example, low, medium, full and high roasts are produced by varying temperature, humidity and amount of time in the roaster. For instance, a high roast produces strong flavors and dark color, while a low roast produces mild flavors and light color. Roasting temperatures vary from 70° C. to 180° C. while roasting times tend to vary from about 30 to 60 minutes.

Normally, cocoa beans are roasted with the shell still on. However, other variations in the roasting process include nib roasting, wherein the shell is first removed by a rapid or moist heating step and liquor roasting.

Winnowing, the next step in the process, is a process of separating the nib or kernel from the inedible shell. This is performed by conventional techniques.

The next step in the preparation of cocoa butter is the grinding of the kernel or nib of the cocoa bean. The nib is a cellular mass which contains 50–56% cocoa fat. The grinding step liberates the fat locked within the cell wall. The nibs are usually ground while they are still warm after roasting. The grinding step is accomplished by using conventional techniques. Two modern apparatuses, in particular, are normally used in the grinding step. One uses a pinmill mounted over a rotary roller refiner. The pinmill grinds the nibs to a coarse but fluid liquor. The liquor is delivered to a roll refiner that reduces the particle size until fine. The second type is a vertical horizontal ball mill. Coarsely ground nib is fed to the base of the vertical cylinder that contains small balls in separate compartments. A central spindle causes the balls to rotate at high speeds, grinding the liquor between them and against the internal wall of the cylinder.

As a result of the processes described hereinabove, chocolate liquor is obtained. The cocoa butter is obtained from the chocolate liquor by subjecting the chocolate liquor to hydraulic pressure using procedures known to one skilled in the art. The cocoa butter obtained by this process is known in the U.S. as prime pure cocoa butter.

There are other processes that are used to prepare cocoa butter. For example, expeller cocoa butter is prepared by the expeller process. In this process, cocoa butter is obtained directly from the whole bean by pressing in a cage press. Expeller butter usually has a stronger flavor and darker color than prime cocoa butter and is filtered with carbon or otherwise treated prior to use. Another process for obtaining cocoa butter is to extract cocoa butter, beans, nibs, liquor cake or fines with an organic non-polar solvent such as hexane. Refined cocoa butter is any one of the above cocoa butters that have been treated to remove impurities and undesirable odors and flavors.

Any of the cocoa butters described hereinabove can be utilized to make the melted cocoa butter used in the present invention or as explained hereinbelow, can be utilized to prepare the partially hydrolyzed cocoa butter emulsion.

Once the cocoa butter is prepared, it is treated to be utilized in the present invention. Cocoa butter is a solid at room temperature (20° C.), starts to soften around 30° C. and melts completely just below the body temperature. Therefore, if cocoa butter is to be used in the medicament, it is first melted. This is accomplished by techniques known in the art, such as by placing the cocoa butter in water that has been heated to temperatures ranging from 100° F. to 212° F. for time sufficient until the cocoa butter melts. The melted cocoa butter is then ready to be utilized directly in the medicament of the present invention.

On the other hand if the medicament is to contain partially hydrolyzed cocoa butter emulsions, the cocoa butter is further treated as described hereinbelow.

"Partially hydrolyzed cocoa butter", as used herein contains cocoa butter that has undergone partial hydrolysis or contains cocoa butter mixed with fully hydrolyzed cocoa butter or contains fully hydrolyzed cocoa butter mixed with cocoa butter having partial hydrolysis of the triglycerides or combination thereof. As described hereinabove, cocoa butter is composed of triglycerides. Complete hydrolysis thereof will hydrolyze all of the ester bonds to form a soap. Partially hydrolyzed cocoa butter is therefore a product that contains partial hydrolysis of the triglycerides.

Thus, partially hydrolyzed cocoa butter contains cocoa butter that has not reacted with the base as well as the cocoa butter that has been fully hydrolyzed. As described hereinabove, partially hydrolyzed cocoa butter is an emulsion. Thus, the term "partially hydrolyzed cocoa butter emulsion" refers to the emulsion product obtained from the partial hydrolysis of melted cocoa butter, i.e., an oil in water emulsion. On the other hand, when reference is made to "partially hydrolyzed cocoa butter," it refers to the oil portion of the emulsion.

Partially hydrolyzed cocoa butter emulsion is prepared by the procedures described in U.S. Pat. Nos. 3,862,197, 3,856,936 and 3,860,702, the contents of which are incorporated by reference. In accordance with the procedures described therein, the partially hydrolyzed cocoa butter emulsion is prepared by partially converting the cocoa butter to a soap by reacting a portion of cocoa butter with an alkali base, such as sodium hydroxide or potassium hydroxide, in a manner insufficient to react all of the cocoa butter so that part of the cocoa butter is unreacted and is not converted to soap. Typically excess base is utilized, so the degree of hydrolysis is controlled by the time of the reaction. The reaction is terminated by the addition of acid to neutralize the remaining base. This hydrolysis reaction described hereinabove by which the cocoa butter is converted to soaps and then to free acids is well known in the art. These are the same reactions by which soaps or free fatty acids have been historically made from natural fats and oils. However, unlike those conventional methods, partially hydrolyzed cocoa butter is only a partial hydrolysis rather than complete hydrolysis conventionally carried out in the manufacture of soap. The resulting soap and unreacted cocoa butter is recovered and treated with a mineral acid, such as hydrochloric acid, in an amount sufficient to react with the soap to form free fatty acids with a portion of unreacted cocoa butter.

Typically, natural cocoa butter is melted by heating in hot water and saponified by the addition of a strong inorganic base, such as sodium hydroxide, potassium hydroxide, and the like, for example, 6N NaOH. The degree of hydrolysis is controlled by the time rate of reaction. The molar ratio of base to cocoa butter in the hydrolysis ranges from about 6:1 to about 36:1, but most preferably from about 12:1 to about 20:1. This mixture is heated, stirred continuously and held at the elevated temperature with stirring until the desired hydrolysis is completed. Preferably, the temperature of the water ranges between 190°–210° F. In addition, the pH of the solution preferably ranges from about 10.0 to 12.0 and more preferably from 10.5 to 11.5, with pH equal to 11.5 being the most preferred. The reaction mixture is held at these conditions until the desired amount of hydrolysis is obtained. For example, the reaction mixture may undergo hydrolysis for about five minutes. This results in an incomplete saponification producing a mixture of unsaponified and saponified cocoa butter. When the desired hydrolysis is complete, the mixture is then acidified with acid such as hydrochloric acid, for example, 6N hydrochloric acid, accompanied by vigorous stirring. Preferably, the pH after initial addition of acid drops to about 2.5. At this point the mixture is washed with water three times to remove salts, excess hydrochloric acid and glycerine, and a soft creamy mass is recovered. The mixture is then raised to a pH of 6.3–6.8 and most preferably to about 6.5.

It is preferred that at the conclusion of the hydrolysis reaction and work-up, the amount of hydrolysis be determined. If additional hydrolysis is required, then the reaction is repeated again. If, on the other hand, the hydrolysis proceeded too far, then additional cocoa butter is added until the desired level is obtained.

Alternatively, partially hydrolyzed cocoa butter emulsion is prepared by mixing cocoa butter with fully hydrolyzed cocoa butter or mixing cocoa butter with partially hydrolyzed cocoa butter or mixing partially hydrolyzed cocoa butter with fully hydrolyzed cocoa butter or combination thereof.

The resulting product is an oil-in-water emulsion which has a white creamy appearance. It is dispersible in water and will mix with water at any level, ranging from 0% to 100% (w/w), inclusive. For instance, it will mix with water at concentrations ranging from 0% to 95% water (w/w). It is preferred that the viscosity of the emulsion at 40° C. ranges from about 0.1 poise to about 1.0 poise and preferably from 0.4 to 0.6 poise. In a preferred embodiment a 10% emulsion has a viscosity at 40° C. of about 0.4 poise, while the viscosity of a 30% emulsion at 40° C. is about 0.6 poise. The emulsion breaks at a temperature range from about 85° to about 100° C. In addition, in a preferred embodiment, the slip melting point of anhydrous partially hydrolyzed cocoa butter is about 43° C.

The emulsion is mostly water ranging from about 70–90% water (w/w) and more preferably about 70–85% (w/w) and most preferably about 70% water. Thus, it is preferred that the amount of partially hydrolyzed cocoa butter (i.e., the oil) present ranges from about 10% to about 30% (w/w) and more preferably about 20 to about 30% (w/w).

The free fatty acids found in the emulsion include mostly palmitic acid, stearic acid and oleic acid. In the non-aqueous phase of the emulsion, the total amount of free fatty acid ranges from about 45% to about 65% (w/w), and more preferably from about 50% to about 60% (w/w) and most preferably at about 56% (w/w). of the amount of free fatty acid, the amount of oleic, stearic and palmitic acids are about the same. Preferably, the amount of palmitic acid in the non-aqueous phase of the emulsion ranges from about 10 to about 20% (w/w), more preferably from about 13 to about 17% and most preferably from about 15 to about 15.5% (w/w). The amount of stearic acid in the non-aqueous phase of the emulsion ranges from about 15% to about 25% (w/w) and more preferably from about 18 to about 22% (w/w) and most preferably from about 19 to about 19.5% (w/w). The oleic acid in the non-aqueous phase of the emulsion preferably ranges from about 17 to about 27% (w/w) and more preferably from about 19 to about 25% (w/w) and most preferably from about 21.5 to about 22.5% (w/w).

The amount of triglycerides, i.e., unsaponified cocoa butter, in the non-aqueous phase ranges from about 30 to about 55% (w/w), and more preferably from about 40 to about 50% (w/w), and most preferably at about 48% (w/w).

It should be noted that unless indicated to the contrary, all percentages of the components recited herein are weight percentages (weight percent) based upon the total weight of the composition.

The medicament of the present invention contains the cocoa butter or partially hydrolyzed cocoa butter emulsion. The compositions of the present invention may also contain other ingredients of the type commonly employed by those skilled in the art for formulating pharmaceutical compositions for topical applications. These may include, for example, carriers, emollients, humectants, surfactants, emulsifying agents, auxiliary emulsifiers, emulsion stabilizing agents, thickening agents, preservatives, chelating agents, pigments, dyes, colorants, perfumes, fragrances, penetration enhancers, gelling agents, and the like.

Any topical formulation known to the skilled artisan, such as solution, suspension, emulsion, lotion, cream, gel, ointment, liposome, aerosol spray, polymeric gel, sol, cataplasm, plaster, pads, film, or tape can be utilized. The medicament may also contain various antibacterial and antifungal agents, for example, parabens, chlorobutanol, phenol, ascorbic acids, thimerosal, and the like. Dispersions can also be prepared using glycerol, liquid polyethylene glycols and the like, and mixtures thereof.

Other ingredients that may be additionally present with the cocoa or partially hydrolyzed cocoa butter emulsion of the present invention include but are not limited to water, glycerine, mineral oil, triethanolamine, glycerol stearate, acetylated lanolin alcohol, fragrance, dimethicone, magnesium aluminum silicate, methylparaben, propylparaben, stearamide AMP, carbomer 934, disodium EDTA, propylene glycol, caramel, and dyes and the like.

These additional ingredients are admixed with cocoa butter and/or partially hydrolyzed cocoa butter emulsion when they are in their melted state. These additives and other ingredients are usually present in amounts ranging from 0.1% to 25% and more preferably from about 0.1% to about 15%.

In addition, the cocoa butter or partially hydrolyzed cocoa butter emulsion may be a coactive ingredient with other active agents useful in treating burns and wounds, such as fructose.

When cocoa butter is the active ingredient, the formulation of the present invention contains from about 0.10% to about 100% cocoa butter (w/w) and most preferably from about 50% to about 100%, and most preferably from about 75% to about 100% (w/w). When partially hydrolyzed cocoa butter emulsion is the active ingredient, it is used in amounts ranging from 0.1% to about 100% (w/w), and more preferably from about 50% to about 100% (w/w). and most preferably from about 75% to about 100% (w/w) However, as indicated hereinabove, the amount of partially hydrolyzed cocoa butter present in the emulsion ranges from about 10% to about 30% (w/w) and most preferably from about 20% to about 30% by weight. The remainder of the emulsion is water, with the water content of the emulsion ranging from about 70–95% water (w/w), more preferably about 70–85% (w/w), and most preferably about 70% (w/w) relative to weight of the oil (i.e., partially hydrolyzed cocoa butter portion). The cocoa butter may be administered without any additional ingredients or may contain the additional ingredients discussed hereinabove.

Inasmuch as cocoa butter is insoluble in water, if an aqueous system is desired, such as in a cream, then an emulsifier must be present. On the other hand, since the partially hydrolyzed cocoa butter emulsion is an emulsion, the presence of an emulsifier therewith is optional.

The amount of emulsifier used can vary depending on the system, but the amount present in cocoa butter formulations when admixed with water or aqueous solvent will be an effective emulsifying amount. In partially hydrolyzed cocoa butter formulations, the amount of emulsion present can vary. In either case, it is preferred that the emulsifier be present as from about 0.1 to 25% by weight of the composition and preferably from about 1 to 10% by weight.

The composition of the present invention may be used in an aerosol spray, in which a propellant is additionally added to the formulation. In this formulation, the propellant is usually present in amounts ranging from 0 to 50% by weight, exclusive and preferably from about 0 to 30%, exclusive. While any of the known propellants may be used in the compositions of the present invention, preferred propellants include the non-halogenated hydrocarbons, particularly the lower boiling hydrocarbons such as $C_3$–$C_6$ and branched chain hydrocarbons, i.e., propane, butane, isobutane and mixtures thereof. Other preferred propellants include the ethers, such as dimethylether, hydrofluorocarbon and the compressed gases such as $N_2$ and $CO_2$.

The medicaments of the present composition are utilized to treat partial thickness burns or wounds as described hereinabove. The preferred burns are thermal burns, such as first or second degree burns. The present compositions of the present invention also can be used to treat solar burns, such as sunburns, especially minor sunburns. The present composition is also useful in treating bedsores, cuts, scratches, scrapes and other wounds, as described hereinabove. The composition of the present invention is applied externally i.e., topically to the injured area. The present invention is utilized to treat the injured area of the skin. If an object is lodged in the skin, it should be removed prior to treatment. The amount of the medicament of the present invention that will be applied as well as duration of the treatment will vary in accordance with parameters well understood by the physician. These parameters include, inter alia, the condition being treated, the extent of the injury, the depth of the injury, the location on the body of the injury, the age, the weight and physical condition of the subject and the like.

However, it is to be understood that the present composition is used to treat the skin injury caused by the burn or wound. It is not meant to treat injuries that may have affected the underlying tissue and organs. In such a case, the cocoa butter or hydrolyzed cocoa butter is admixed with other active ingredients.

The cocoa butter or partially hydrolyzed cocoa butter composition of the present invention is, applied topically and directly to the burns or wound. When the wound is deep, or the burn severe, it is preferred that the composition is in the form of an ointment, salve or cream which is spread directly onto the wound and then covered with a standard sterile dressing pad or other appropriate dressing material. Alternatively, the ointment, cream or salve of the present composition is applied directly onto the dressing pad or other appropriate dressing material as if spreading peanut butter on a slice of bread. The pad or dressing material is then placed over the wound or burn with the medicine-side down. This latter approach works better when applying dressing to severe burns and shallow wounds. For first degree burns and slight abrasions, in addition, the composition may be applied as an aerosol.

That is to say, the medicine is applied to a wound so as to cover the injured surface completely, e.g., with one-quarter inch thickness of the medicine. Dressing-change schedules are dictated by the condition of the wound. In highly-contaminated (pussy) or weeping wounds or severe burns, dressing changes may be performed every four to six hours; in other wounds or burns, changes are performed less frequently, sometimes only one or two times per day.

Dressings are advantageously changed three to four times a day. Repeated daily dressing changes are continued until the wound or burn is healed. Healing time varies, depending upon the type and depth of the wound or the severity of the burn.

The present medicinal composition is effective in the treatment of a large variety of wounds and burns to man where bacterial and fungal contamination ordinarily occur. The present medicinal composition can also be used to treat burns and wounds in other mammals, such as dogs, cats, horses, farm animals, and the like. Using the composition of the present invention, there is rapid healing.

To a large extent, the thus treated wounds or burns heal with no scars or with minimal scarring. Antibiotics may be used in conjunction with the medicine, but are not required.

The subject composition is an effective medicine which is useful in the treatment of various burns and wounds. They include inter alia the following:

1. Burns (infected and non-infected)
    Thermal burns
    (a) First degree
    (b) Second degree
2. Abrasions (infected and non-infected)
3. Deep wounds (infected and non-infected)
4. Gunshot wounds (infected or non-infected)
5. Lacerations (infected and non-infected)
6. Bedsores (infected and non-infected)
7. Open wounds to bone (infected and non-infected).

The present invention will now be described with reference to the examples which follow. It should be noted, however, that the present invention is not deemed to be limited only to these examples.

EXAMPLE 1

Partially Hydrolyzed Cocoa Butter Emulsion

Pure cocoa butter in water was melted by heating to 190° F., sufficient 6N NaOH was added to raise the pH of the mixture to 11.5 thereto. The temperature was raised to 210° F. as the mixture was stirred. The pH of the solution was 11.5 at the end of five minutes. The basic mixture was neutralized with sufficient 6N HCl until the pH became 2.5. The mixture was rinsed three times with 190° F. water. The pH was increased to 6.5 with the addition of 6N NaOH. An emulsion was formed at 190° F. and the water content was adjusted to the desired concentration.

The percent H$_2$O present in the product was 70% (w/w). The percent of individual free fatty acids ncluding the Na salts of the free fatty acids in the on aqueous phase of the product was;

| | |
|---|---|
| Palmitic | 15.3% (w/w) |
| Stearic | 19.2% (w/w) |
| Oleic | 22.0% (w/w) |

Then the total free fatty acids including the Na salts was 56% (w/w) and the amount of triglycerides left in the non-aqueous phase of the emulsion was 48% (w/w).

EXAMPLE 2

The purpose of this study was to examine the effect of cocoa butter and partially hydrolyzed cocoa butter on second-degree burn and partial thickness wound healing. White specific pathogen free (SPF) pigs were selected for the experimental animal because of the morphologic and functional similarity of their skin to human skin.

Materials and Methods

Experimental Animals

Four young specific pathogen free (SPF) pigs weighing 20–25 kg were conditioned for two weeks prior to experimentation. Two animals received partial thickness wounds and the other two animals received second-degree burn wounds. The animals were given water and a basal diet without antibiotics (Purina Control Factor) ad libitum and housed individually in animal facilities meeting American Association for Accreditation of Laboratory Animal Care [AAALAC] compliance with controlled temperature (19°–21° C.) and light and dark (12h/12h LD).

Animal Preparation

The experimental animals were clipped with standard animal clippers. The skin on the back and both sides of the animal was prepared for wounding by washing with a non-antibiotic soap (Neutrogena®). Anesthesia was induced by intramuscular injection of ketamine hydrochloride (20 mg/kg) and maintained by mask inhalation of isoflurane and oxygen combination.

Partial Thickness Wounds

Approximately one hundred rectangular wounds measuring 10×7 and 0.3 mm deep were made in the paravertebral and thoracic area with a specialized electrokeratome fitted with a 7 mm blade. Each treatment group contained thirty-five to forty wounds. Wounds were assigned to one of the following treatment groups:

| Number of Animals | Treatment Groups |
|---|---|
| 2 | Air Exposed (control), Pure Cocoa Butter, Partially Hydrolyzed Cocoa Butter |

Before application of the treatments, the wounds were blotted dry. Treatments were applied daily for the first five days post wounding.

Epidermal Migration Assessment (Partial Thickness Wounds)

On Days 2–6, five wounds from each treatment group were surgically excised using an electrokeratome (0.6 mm deep). Any specimens that were not excised intact were discarded. The excised wounds and the surrounding normal skin were incubated in 0.5M NaBr for 24 hours at 37° C. After incubation the specimens were separated into epidermal and dermal sheets. The epidermis was examined macroscopically for defects in the area of the wounds. Epithelization was considered complete if no defect were present (healed); any defect in the area indicated that healing was incomplete. The epidermal sheet was then placed on cardboard for a permanent record.

Second-Degree Burn Wounds

The pig was anesthetized as above and four specially designed cylindrical brass rods weighing 358 g each were heated in a boiling water bath to 100° C. A rod was removed from the water bath and wiped dry before it was applied to the skin surface to prevent water droplets from creating a steam burn on the skin. The brass rod was held at a vertical position on the skin for six seconds, with all pressure supplied by gravity, to make a burn wound 8.5 mm diameter×0.8 mm deep. Immediately after burning, the roof of the burn blister was removed with a sterile spatula. The burn wounds were approximately 2 cm from each other.

Approximately one hundred burn wounds were made on the anterior two-thirds of the animal. The posterior third of the animal could not be used because of anatomical differences in burn wound healing (a more rapid healing of burns has been seen there). Burn wounds were assigned to one of the following treatment groups: 1) air exposed control, 2) pure melted cocoa butter, or 3) partially hydrolyzed cocoa butter emulsion prepared in accordance with the procedure in Example 1. Burns were treated once daily for the first five days.

Edidermal Migration Assessment (Burn Wounds)

Beginning on Day 7 after wounding (Day 0) and each day thereafter for six days, six wounds and the surrounding normal skin from each treatment area were excised and evaluated as described for the partial thickness wound healing assessment.

Results

The number of wounds healed (epithelized) was divided by the total number of wounds sampled per day ad multiplied by 100 (Tables 1 and 2). The percentage of the wounds healed was then plotted against the days after wounding (FIGS. 1 and 2).

Partial Thickness Wounds

Days 2 and 3

None of the wounds in any of the treatment groups showed complete epithelization.

Day 4

The partially hydrolyzed cocoa butter emulsion treated wounds showed the highest percent of wounds completely epithelized (90%). This was followed by the pure cocoa butter treated wounds which were 80% completely epithelized on the same day; whereas the air exposed wounds were 50% completely epithelized.

Day 5

Wounds from all treatment groups were 100% epithelized.

Second-Degree Burn Wounds

Day 7

Burn wounds treated with the partially hydrolyzed cocoa butter emulsion were 100% completely epithelized as compared to burn wounds treated with pure cocoa butter and exposed air which were 40% and 0%, respectively, completely epithelized.

Days 8 and 9

Both the partially hydrolyzed cocoa butter emulsion and pure cocoa butter showed 100% complete epithelization. None of the air exposed burn wounds were completely epithelized on these days.

Day 10, 11 and 12

The air exposed burn wounds initiated complete epithelization on day 10 post burning (10%). On days 11 and 12 air exposed burn wounds were 60% and 100% completely epithelized, respectively.

The results of both these studies show that in both the burn and partial thickness wound studies, wounds that were treated with the partially hydrolyzed cocoa butter emulsion showed the highest percentages of complete epithelization. The pure cocoa butter also appeared to enhance the rate of epidermal migration as compared to air exposed control wounds in both studies. No differences in the rate of epidermal coverage was established between the partially hydrolyzed cocoa butter emulsion and pure cocoa butter formulations with the partial thickness study; however, the second-degree burn study appeared to reveal differences in the rate of healing between the two formulations.

TABLE 1

THE EFFECT OF PARTIALLY HYDROLYZED AND PURE COCOA BUTTER ON PARTIAL THICKNESS WOUND HEALING (two animals)*

| | DAYS AFTER WOUNDING | | | | | |
|---|---|---|---|---|---|---|
| TREATMENT | 2 | 3 | 4 | 5 | 6 | 7 |
| Air Exposed Control | 0/10 (0%) | 0/10 (0%) | 5/10 (50%) | 10/10 (100%) | 10/10 (100%) | 10/10 (100%) |
| Pure Cocoa Butter | 0/10 (0%) | 0/10 (0%) | 8/10 (80%) | 10/10 (100%) | 10/10 (100%) | 10/10 (100%) |
| Partially Hydrolyzed Cocoa Butter Emulsion | 0/10 (0%) | 0/10 (0%) | 9/10 (90%) | 10/10 (100%) | 10/10 (100%) | 10/10 (100%) |

*Data is presented as number of wounds healed over number of wounds sampled.
( ) Percent of wounds epithelized

TABLE 2

THE EFFECT OF PARTIALLY HYDROLYZED AND PURE COCOA BUTTER ON SECOND-DEGREE BURN WOUND HEALING (two animals)*

| | DAYS AFTER WOUNDING | | | | | |
|---|---|---|---|---|---|---|
| TREATMENT | 7 | 8 | 9 | 10 | 11 | 12 |
| Air Exposed Control | 0/10 (0%) | 0/10 (0%) | 0/10 (0%) | 1/10 (10%) | 6/10 (60%) | 10/10 (100%) |
| Pure Cocoa Butter | 4/10 (40%) | 10/10 (100%) | 10/10 (100%) | 10/10 (100%) | 10/10 (100%) | 10/10 (100%) |
| Partially Hydrolyzed Cocoa Butter | 10/10 (100%) | 10/10 (100%) | 10/10 (100%) | 10/10 (100%) | 10/10 (100%) | 10/10 (100%) |

*Data is presented as number of wounds healed over number of wounds sampled.
( ) Percent of wounds epithelized The above preferred embodiments and examples are given to illustrate the scope and spirit of the present invention. These embodiments and examples will make apparent to those skilled in the art other embodiments and examples. These other embodiments and examples are also within the contemplation of the present invention. Therefore, the present invention should only be limited by the appended claims.

What is claimed is:

1. A method for treating a partial thickness thermal burn to the skin of a warm-blooded animal comprising applying topically to the locus of the skin that is injured a medicament comprising as the active ingredient a burn-healing effective amount of cocoa butter.

2. The method according to claim 1 wherein the medicament contains from about 75% to about 100% w/w of cocoa butter.

3. The method according to claim 1 wherein the thermal burn is first or second degree burn.

4. The method according to claim 1 wherein the warm-blooded animal is a mammal.

5. The method according to claim 4 wherein the mammal is a human being.

6. A method for treating a partial thickness thermal burn to the skin of a warm-blooded animal comprising applying topically to the locus of the skin that is injured a medicament comprising as the active ingredient a burn-healing effective amount of partially hydrolyzed cocoa butter emulsion.

7. The method according to claim 6 wherein the partially hydrolyzed cocoa butter emulsion contains about 10% to about 30% partially hydrolyzed cocoa butter (w/w) and about 70 to about 90% water (w/w).

8. The method according to claim 7 wherein the partially hydrolyzed cocoa butter emulsion contains about 20% to about 30% partially hydrolyzed cocoa butter (w/w).

9. The method according to claim 6 wherein said partially hydrolyzed cocoa butter emulsion contains in the non-aqueous portion about 4 to about 6% by weight stearic acid, about 4.5 to about 6.5% by weight oleic acid, about 3 to about 4.5% by weight palmitic acid and about 10 to about 15% by weight triglycerides.

10. The method according to claim 6 wherein the medicament contains from about 75% to about 100% by weight partially hydrolyzed cocoa butter emulsion.

11. The method according to claim 6 wherein the thermal burn is first or second degree burn.

12. The method according to claim 6 wherein the warm-blooded animal is a mammal.

13. The method according to claim 12 wherein the mammal is a human being.

14. A method for treating a partial thickness wound to the skin of a warm-blooded animal comprising applying topically to the area of the skin which is injured a medicament comprising as the active ingredient a wound healing effective amount of cocoa butter.

15. The method according to claim 14 wherein cocoa butter is present in amounts ranging from about 75% to 100% (w/w).

16. The method according to claim 14 wherein the wound is an incised wound, a lacerated wound, a penetrating wound, a perforated wound, a puncture wound, an open wound, or a subcutaneous wound.

17. The method according to claim 14 wherein the warm-blood animal is a mammal.

18. The method according to claim 17 wherein the mammal is a human being.

19. A method for treating a partial thickness wound to the skin of a warm-blooded animal comprising applying topically to the area of the skin which is injured a medicament comprising as the active ingredient a wound-healing effective amount of partially hydrolyzed cocoa butter emulsion.

20. The method according to claim 19 where the partially hydrolyzed cocoa butter emulsion contains about 10% to about 30% by weight partially hydrolyzed cocoa butter and about 70% to about 90% by weight water.

21. The method according to claim 20 wherein the partially hydrolyzed cocoa butter emulsion contains about 20% to about 30% by weight partially hydrolyzed cocoa butter.

22. The method according to claim 19 where said partially hydrolyzed cocoa butter emulsion contains in the non-aqueous portion about 4 to about 6% by weight stearic acid, about 4.5 to about 6.5% by weight oleic acid, about 3 to about 4.5% by weight palmitic acid, and about 10 to about 15% by weight triglycerides.

23. The method according to claim 19 wherein the medicament contains from about 75% to about 100% by weight partially hydrolyzed cocoa butter emulsion.

24. The method according to claim 19 wherein the wound is an incised wound, a lacerated wound, a penetrating wound, a perforated wound, a puncture wound, an open wound or, a subcutaneous wound.

25. The method according to claim 19 wherein the warm-blooded animal is a mammal.

26. The method according to claim 25 wherein the mammal is a human being.

* * * * *

UNITED STATES PATENT AND TRADEMARK OFFICE
CERTIFICATE OF CORRECTION

PATENT NO. : 5,837,227
DATED : November 17, 1998
INVENTOR(S) : Barry L. Zoumas, et al.

It is certified that error appears in the above-identified patent and that said Letters Patent are hereby corrected as shown below:

Column 5, line 66: "of" should read --Of--

Column 10, line 28: "Edidermal" should read --Epidermal--

Signed and Sealed this

Eighteenth Day of January, 2000

Attest:

Q. TODD DICKINSON

*Attesting Officer*  *Commissioner of Patents and Trademarks*